(12) United States Patent
Berman et al.

(10) Patent No.: US 7,684,022 B2
(45) Date of Patent: Mar. 23, 2010

(54) SYSTEM AND METHOD FOR SHADE SELECTION USING A FABRIC BRIGHTNESS FACTOR

(75) Inventors: Joel Berman, Hewlett, NY (US); Jan Berman, Wilton, CT (US)

(73) Assignee: Mechoshade Systems, Inc., Long Island City, NY (US)

( * ) Notice: Subject to any disclaimer, the term of this patent is extended or adjusted under 35 U.S.C. 154(b) by 634 days.

(21) Appl. No.: 11/539,559

(22) Filed: Oct. 6, 2006

(65) Prior Publication Data

US 2007/0291252 A1 Dec. 20, 2007

Related U.S. Application Data

(60) Provisional application No. 60/804,694, filed on Jun. 14, 2006.

(51) Int. Cl.
*G01N 21/00* (2006.01)
(52) U.S. Cl. .................. 356/73; 356/402; 356/432; 356/445; 250/559.01; 250/559.11; 442/59; 442/301; 442/312
(58) Field of Classification Search ............ 250/559.01, 250/559.11; 356/73, 429, 432–435, 445, 356/2; 442/59, 68–76, 304–312
See application file for complete search history.

(56) References Cited

U.S. PATENT DOCUMENTS

2005/0215147 A1* 9/2005 Masters et al. ............... 442/59
2007/0248246 A1* 10/2007 Cherkassky et al. ......... 382/111

* cited by examiner

*Primary Examiner*—Gregory J Toatley, Jr.
*Assistant Examiner*—Iyabo S Alli
(74) *Attorney, Agent, or Firm*—Snell & Wilmer L.L.P.

(57) ABSTRACT

A system and method for determining a brightness factor associated with a window shade fabric is disclosed. The brightness factor incorporates the openness factor of the fabric, visible light reflectance of the fabric and visible light transmission of the fabric. The brightness factor helps to determine the optimum window shade fabric for a particular room, building or other location. The brightness factor information may be used to select the correct fabric based on desired interior function, light level, the relative surface brightness, and/or any other desired interior characteristic. The fabric selection may affect the building envelope by, for example, facilitating the optimization of daylighting, reduction of artificial electric lighting needs, and minimization of glare conditions.

18 Claims, 5 Drawing Sheets

SYSTEM AND METHOD FOR SHADE SELECTION USING A FABRIC BRIGHTNESS FACTOR

CROSS REFERENCE TO RELATED APPLICATIONS

This application claims priority to, and the benefit of, U.S. Provisional Application Ser. No. 60/804,694, filed Jun. 14, 2006 and entitled "System and Method For Shade Selection Using a Fabric Brightness Factor", which is hereby incorporated by reference in its entirety.

FIELD OF THE INVENTION

The invention generally relates to the optimum selection of a window shade, and more particularly, to the use of a brightness factor for selecting the optimum window shade.

BACKGROUND OF THE INVENTION

Incorporating the appropriate window shades over certain windows can make a substantial difference in the aesthetics, comfort and energy savings in a room. In that regard, window shades are often utilized for a variety of purposes such as, for example, maximizing a view, maximizing daylight, blacking out a room, minimizing brightness, adjusting to climatic variables and sky conditions, minimizing heat at certain times of the year, maximizing heat during other times of the year, protecting work surfaces, minimizing glare and protecting people from direct sun.

When choosing the appropriate window shade system, lighting designers and interior architects typically consider various factors such as, for example, glazing (glass) properties, room properties and environmental conditions. The glass properties may include total solar and visible properties (transmission, reflection, absorption), single or multiple pane glass, chemicals or materials between the panes of glass, angled glass, tint, sun screens, UV transmission, bars over the windows, frosted glass and the like. The room properties may include the interior lighting and the reflectance from the wall, floor and ceiling. The environmental conditions may include typical solar or climate conditions (e.g., often cloudy in Seattle, often clear skies in Phoenix, etc.), obstructions (mountains, trees, other buildings, etc.), luminance (the amount of light leaving a point on a surface in a given direction (e.g., that comes to the eye from a surface)) and illuminance (the amount of visible light on a surface from all directions above that surface or the density of luminous flux incident on a surface). Luminance is measured in Footlamberts, Candala/Square Meter, Nits, or Lambert. Illuminance is measured in Lux, Footcandle or Lumen/Square Meter. The impact of a window shade system on a particular room may also be calculated under various conditions. For example, measurements may be obtained related to the luminance from the shade, walls and ceiling, the amount of light through the shade and glass, etc.

In recent years, corporate and institutional building design includes higher and higher visual light transmission glass for allowing more natural daylight into the building space, enhancing the view to the outside and using the daylight to reduce artificial lighting and A/C energy usage. Such increasing use of higher visual light transmission glass creates both problems and opportunities.

Since around the year 2000, designers have changed their selection of building glazings to low E clear glass, Starfire (no iron) glass, or a similar tinted low E glazing. Such glazings have the highest ratio of visible light transmission (VLt) to Solar Heat Gain Factor (SHGF). Over the years, the VLt of double glazing has changed from a low of 0.20 (low E solar ban), to an uncoated bronze or gray heat absorbing glass of 0.40 VLt, to low iron glass (green, blue aqua) with a VLt of 0.6 and now to a low E clear on Starfire glass with a VLt of 0.70-0.75. The SHGF percentage of heat inside the glass with a low E coating has remained at +/−0.40-0.55. In other words, the ratio of heat gain to VLt through the glass was previously close to a 1:1 ratio, but the ratio is now +/−1:1.75, which is a dramatic increase of VLt over heat gain.

Based in part on the lower heat gain, the HVAC systems have been down sized. However, the HVAC systems have not been sufficiently adjusted for the substantial gain in VLt which also has a strong direct solar radiant component.

Moreover, in an effort to reduce glare and limit the impact of transient adaptation of the eye as the eye goes from one area (the task) to another area (adjacent surroundings or surfaces), lighting designers have determined an appropriate ratio for the perceived and measured brightness inside a person's field of view. Adjacent surfaces are within a 30 degree visual cone and non-adjacent surfaces are within a 30-60 degree cone. (a person's field of view is generally considered to be a 60 degree visual cone). The recommended ratio between task and adjacent surroundings is 3:1, the recommended ratio between task and remote surroundings is 10:1, and the recommended ratio should be 40:1 for everything outside the 60 degree cone. These ratios are applicable for areas on the order of one steradian, so higher ratios are recommended in small areas to add visual interest.

To provide an example of the ratios, if the work surface has 50 foot candles (FC), then the visual zone should not have any glare or brightness that exceeds 500 FC within remote surroundings, namely within the 1:10 ratio. In the case of a computer screen, if the lumen output of the screen is 200 Candela M/2, then the maximum amount of brightness in the person's field of view should not be more than 2000 Candela M/2 within remote surroundings.

As the VLt of the glass increases and as lighting designers attempt to control the brightness inside a person's field of view, the shade cloth color on the outside of the building also has an effect on the building design, along with the uniformity and alignment of the window covering. As such, the impact of the window covering is now becoming an integral element in building design.

To calculate the heat flow through the glass by convection and direct radiation, an ASHRAE (American Society of Heating, Refrigerating and Air-Conditioning Engineers, Inc.) formula using the solar optical properties of the fabric is used to calculate SHGF of the glass, along with the glass and shade combination. Currently, the available performance data for a screen fabric are Total Solar Reflectance (TSr); Total Solar Transmission (TSt); and Total Solar Absorbtion (TSa), wherein the total of TSr+TSt+TSa=100%. Other performance data includes Visible Light Transmission; UV Transmission and Openness Factor (Fabric Density); however, Visible Light Transmission; UV Transmission and Openness Factor are not included in the ASHRAE formula as they are not components of the total solar measurements used above to develop the SHGF. The SHGF provides the necessary information for calculating heat flow into the building to enable mechanical engineers to more effectively size the HVAC systems.

However, the SHGF does not address the comfort factors of direct solar radiation, or visual brightness near the window wall (i.e., 15-20 feet from the window wall). The engineering standards of the shading coefficient, solar heat gain factor, or solar factor do not include a valuation of comfort at the window wall for the occupant. As such, the tests were conducted to determine the factors that effect personal comfort near a window wall with sun screens. The tests matched different types and kinds of glass with a variety of woven sun screen fabrics, then measured the total heat gain, solar radiation, heat gain and visible light transmission. The tests resulted in a method for determining a screen cloth's "personal comfort value" under reasonable interior environmental conditions with glazing of a specific VLt and/or SHGF.

While various factors, tests and calculations exist for determining the optimum window system, the SHGF and the personal comfort values still do not include the relative brightness (illuminance) of the fabric when it is solar lit, its effect on the interior environment and its impact on the viewers. A strong need exists to compare the surface brightness of different fabrics with a uniform light source to determine the relative brightness of one screen fabric to another screen fabric. A strong need also exists to determine the illuminance or brightness value of a screen on the project such that the factor can help determine the optimum window shade fabric for a particular room, building or other enclosure.

SUMMARY OF THE INVENTION

The present invention includes a system and method for determining a brightness factor associated with an illuminated window shade fabric to help determine the optimum window shade fabric for a particular room, building or other enclosure. The brightness factor incorporates the openness factor of the fabric, visible light reflectance of the fabric and visible light transmission of the fabric. The brightness factor information of the present invention may be used by architects, designers, engineers and the like to select the optimum fabric based on desired interior function, light level, the relative surface brightness, and/or any other desired interior lighting characteristic. The fabric selection may effect the building envelope by, for example, facilitating the optimization of daylighting, reduction of artificial electric lighting needs, and minimization of glare conditions.

BRIEF DESCRIPTION OF THE DRAWING FIGURES

Additional aspects of the present invention will become evident upon reviewing the non-limiting embodiments described in the specification and the claims, in conjunction with the accompanying figures, wherein like numerals designate like elements, and wherein:

DETAILED DESCRIPTION OF EXEMPLARY EMBODIMENTS

Figure 1:
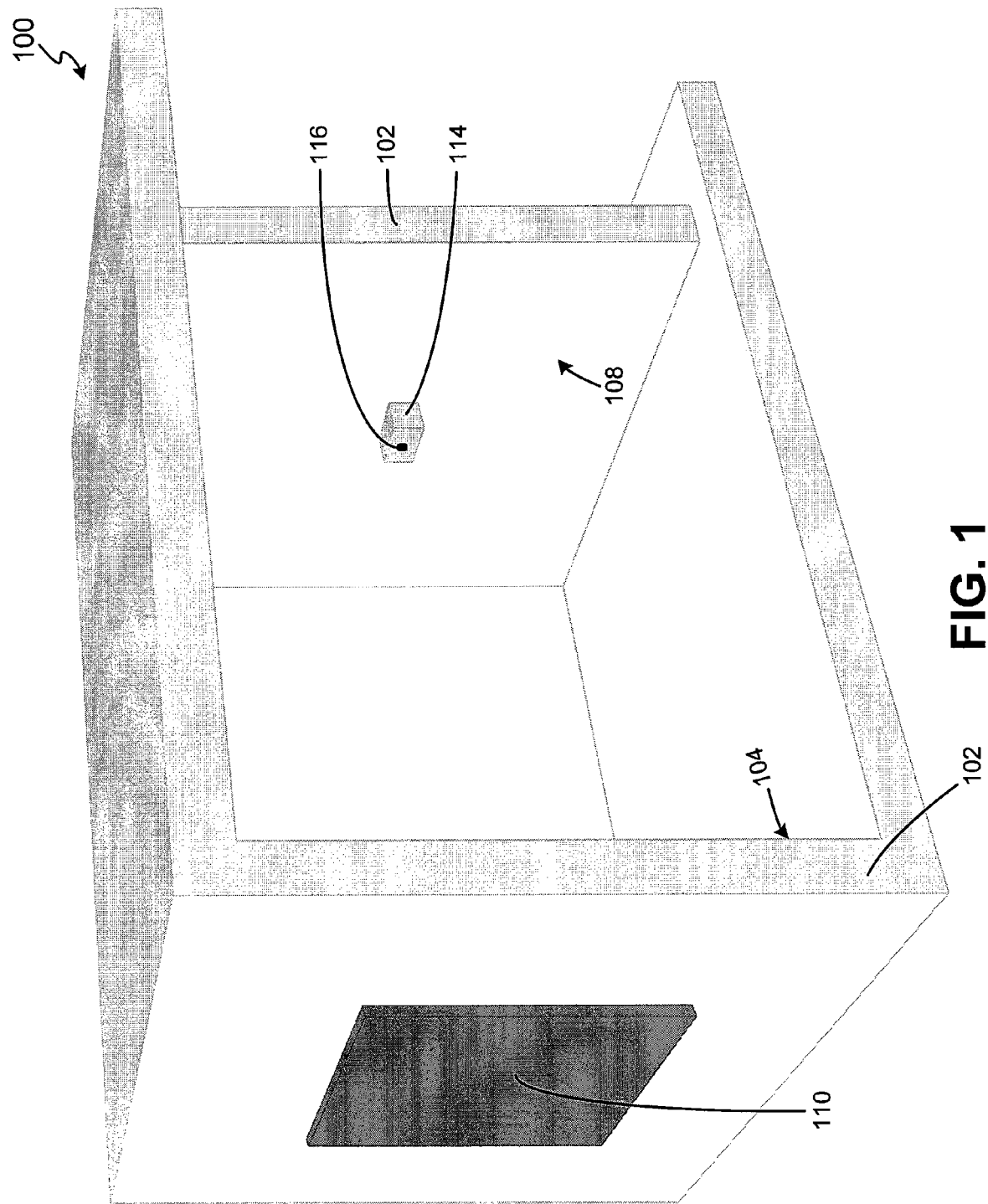
FIG. 1 is an exemplary test chamber to facilitate testing and/or validation of one or more window coverings in accordance with an embodiment of the present invention.

The detailed description of exemplary embodiments of the invention herein shows the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

The present invention generally includes a system and method for determining the brightness factor of a fabric to help lighting designers, interior architects or other professionals to select the optimum fabric for a particular window, room, building or other location. The fabric selection may effect the building envelope by, for example, facilitating the optimization of daylighting, reduction of artificial electric lighting needs, and minimization of glare conditions. The brightness factor data of the present invention may be used by architects, designers, engineers and the like to select the most appropriate fabric based on desired interior function, light level, the relative surface brightness, and/or any other desired interior lighting characteristic. The brightness factor value is critical to the environment and energy efficiency. The brightness factor also provides benefits based on the changes in glazing and the requirements for more and improved energy efficient and sustainable designs.

While factors such as glazing properties, room properties and environmental conditions may be relevant for selecting a window shade system, the selection of the window shade fabric may include different factors. An exemplary embodiment includes determining a brightness factor for a particular illuminated window shade fabric, wherein the brightness factor incorporates the openness factor of the fabric, visible light reflectance of the fabric and visible light transmission of the fabric. The selection of an appropriate fabric for a project should include the proper evaluation of its solar optical properties, color (darker colors reflect more), visible light transmission, and openness factor (fabric density), along with the solar characteristics of the glass and the orientation of the window. The invention includes a system and method for designers and engineers to look at the solar optical properties and characteristics of a screen fabric, along with the relative brightness of the screen fabric under given backlit conditions in relation to other screen fabrics backlit with the same amount of light. In other words, the invention enables designers and engineers to conduct a direct comparison of all screen cloths illuminance characteristics using the brightness factor value.

In addition to comparing different fabrics illuminance under the same backlight conditions, the brightness factor value is also a tool for the lighting designer. The lighting designer may combine the published brightness factor values with the glazing data to determine (in Foot Lamberts, or Foot Candles) the amount of illuminance a given fabric will emit and its effect on the interior illumination, daylighting and surface brightness. For comparison, a typical sky condition without direct sun is about 8,000-9,000 FC, and the sun is about 13,000 FC. In one embodiment, the brightness factor ranges from 0-800, and for roller shade fabrics with different glazing systems, the brightness factor ranges from 0-250.

The brightness factor value can be applied to any screen cloth fabric. Utilizing the existing test data of the solar optical properties, along with fabric construction factors, the standard illuminance of any screen fabric can be developed and compared to other screen fabrics. The brightness factor value provides a relative brightness comparison or lighting output from the inner surface of the product (e.g., window shade), plus the illuminance data to determine the interior brightness level with different amounts of light and different types of glass. One skilled in the art will appreciate that the brightness factor and methods discussed herein may be used with any product or surface; however, the specific embodiment of a window shading system will be discussed herein in more detail.

The use of the brightness factor along with other factors and systems discussed herein to optimize the window shade selection may enhance the visual comfort of occupants of a space. As used herein, the phrase visual comfort includes the absence and/or minimization of physiological pain, irritation and/or distraction. Visual comfort within a space depends on the contrast levels and luminance variations across the space. For example, glare is one of the most common causes of visual discomfort and can result in the occupant having to react to the existing lighting system. The reaction may include turning, moving, or otherwise adjusting the window covering. Surface brightness is an attribute of visual perception in which a surface appears to emit a given amount of light. Brightness is dependent upon the illuminance of a surface and upon the surface reflectivity. Perceived brightness is not linearly proportional to the reflectivity.

The process of developing and verifying the brightness factor value utilized many combinations of solar characteristics and formula in many trial and test combinations. The optimum formula is:

$$BF = (Of + (Vri \times FDP)) \times 1000 = \text{Foot Lamberts or}$$

$$BF = (Of + (Vri \times (Vlt - Of))) \times 1000 = \text{Foot Candles}$$

of brightness or illuminance of the fabric, wherein:

BF=the fabric brightness factor

Vri=Visual Light Reflectance to the interior

Vlt=Visual Light Transmission (i.e., all rays entering the room)

OF=Openness factor (i.e., non-diffused rays entering the room)

FDP=Fabric Diffusion Property (Vlt−OF).

More particularly, fabric diffusion property (FDP) is related to the actual quantity of diffuse light transmission through the fabric material. The lower the FDP, the higher the absorption and reflection of the fabric material. For example, a dark colored fabric will have very little transmitted diffuse light through the fabric material. While dark colors provide a better view through the shadecloth to the outside, dark colors absorb light and heat and are less energy efficient than lighter colors. Dark colors transmit less light and have a lower surface brightness which lowers reflectivity and provides better glare reduced environments for CRTs and work stations. In contrast, light colors are brighter when sunlit which causes high surface brightness and transmission of excessive, debilitating light to workstations. Light colors are difficult to see through due to surface brightness and higher reflectance and transmittance characteristics.

Moreover, the light transmission through fabric during overcast sky conditions is much different than on clear sky conditions. The light from overcast conditions is similar to light through diffusing material (e.g., Plexiglas). As such, the light coming through open areas of the fabric will still be diffuse, thereby limiting light penetration into the building compared to clear sky conditions.

The openness factor (OF) is a shade fabric property, but is also a percentage of the measured visible transmittance value. OF of an illuminated window shade fabric is calculated, in one embodiment, by placing the fabric over one end of a blackened tube, then placing a light meter at the other end of the blackened tube (a blackened tube eliminates or minimizes the affects of the transmittance of the fabric). The light meter measures the visible light through the fabric in BTU per hour per square foot (or Watt per square meter). The light meter then measures the direct visible light without the fabric in its path. The measurements are then compared to determine the reduction in visible light from the illuminated window shade fabric which is considered the openness factor. In an exemplary embodiment, the invention contemplates a visibly transparent fabric with different degrees of openness. The invention may also include translucent fabric with zero or minimal openness, but including visible light reflectance and visible transmittance.

The openness factor property is incorporated into the visible transmittance, so the openness factor reduces the overall brightness factor value too much when the fabric sample under consideration has a low openness factor. As such, in one embodiment, the openness factor is removed from the visible light transmission. For example, a fabric that has a 0.01 openness factor would have a very low brightness factor, when in reality it could have a high brightness factor because of the visible light transmittance. In other words, the openness factor being included in the brightness factor equation may create a weighting factor that distorts the end results. However, the openness factor may remain in the brightness factor equation due to the significant impact of direct solar radiation through the glazing and fabric open areas on the amount of luminance to the interior space.

The visible light reflectance includes the reflection of the internal light off of the inside (interior) surface of an illuminated window shade fabric. The visible light reflectance is determined, in one embodiment, by pointing the light meter at the fabric, then measuring the reflectance off of the fabric. Another measurement is obtained from measuring the direct visible light using the same light meter. The measurements are then compared to determine the reduction in visible light from the reflection off of the window shade fabric, which is considered the visible light reflectance.

The visible light transmission includes the amount of light from outside solar radiation. The visible light transmission of an illuminated window shade fabric is determined, in one embodiment, by placing the fabric over one end of a tube, then placing a light meter at the other end of the tube (a blackened tube is not used when determining the visible light transmission). The light meter measures the visible light through the fabric. The light meter then measures the direct visible light without the fabric in its path. The measurements are then compared to determine the reduction in visible light from the window shade fabric, which is considered the visible light transmission.

In an exemplary embodiment, the determination of the brightness factor is independent of the glass and the solar conditions, but the brightness factor is used in conjunction with the glazing properties when choosing the optimum roller shade fabric. Moreover, in conjunction with a brightness factor, the visible light reflectance of the walls, floor, ceiling, furniture, art work and other components of the room may be used to choose a shade fabric that will work best with a particular project. For example, if the walls, ceiling, floors and furniture are bright and reflective, it may be best to choose a shade fabric with a lower brightness factor. Similarly, if the walls, ceiling, floors and furniture have a medium color value and low reflectance, it may be best to choose a shade fabric with a higher brightness factor.

The brightness factor facilitates a prediction, with other similar screen fabrics, of the approximate brightness of the fabric in Candela M/2 with a specific light source behind the fabric, with or without a glazing. The brightness value is then adjusted with the glazing to be used. For example, 60% visible light transmission glazing compared to 90% visible light transmission or 100% visible light transmission as the case may be.

A window shade or fabric manufacturer or distributor may publish all of its fabrics with all solar and visible light optical proprieties, along with the brightness factor of each fabric and the resultant brightness in Candela M/2 or FC. Any other fabric can either be compared based on similar optical proprieties.

To confirm that the optimum shade fabric was selected and validate the brightness factor, the lighting designer and/or interior architect may determine the impact of the window shade system on a particular room under various conditions. For example, they may obtain measurements related to the illuminance on the shade, walls and ceiling, the amount of light through the shade and glass, etc. to determine if the fabric selection was successful for optimizing daylighting and minimizing glare conditions. After obtaining the optimum window shade fabric based on the brightness factor of the present invention, lighting designers and interior architects may evaluate the level of window brightness and/or identify unusual glare or shadow conditions from adjacent buildings. For example, a north-facing window looking at a south-facing mirror facade often overheats the north elevation and certain laws or ordinances may require the offending building to pay for the increase in energy, etc.

The present invention may interface with or share data with a shade control system, daylighting control system, daylight-brightness control system, daylighting prediction program (e.g., draws a room and calculates brightness areas) (e.g., Radiance), building control system and/or the like. Such systems may include automated shade systems that employ, for example, one or more algorithms to provide appropriate solar protection from direct solar penetration; predict an estimated amount of office illumination; reduction in solar heat gain; reduction in radiant surface temperatures (of the window wall); controlled penetration of the solar ray, optimization of the interior natural daylighting of a structure and optimization of the efficiency of interior lighting systems. For additional information related to automated shade control systems, see U.S. patent application Ser. No. 11/162,377, by inventors Joel Berman, et al., which is entitled "Automated Shade Control Method And System," the entire contents of which is hereby incorporated by reference.

In an exemplary embodiment, such control systems may use the brightness factor data in its programs in conjunction with, for example, the solar angles and brightness on the glass. This information may facilitate determining if it is or is not necessary to move the shades down past the position of the solar ray penetrating the window into the space of the shades because the calculations have determined that too much brightness will come in through the un-shaded window. In one embodiment, the various control systems control the shading system based on the solar position and overrides the brightness factor input (e.g., brightness factor is a secondary control factor). The control system adjusts the shading system to block out the sun, reflection, etc; however, if the sun is not a concern at a particular time, then the control system analyzes the brightness factor to optimize the room conditions.

The invention facilitates the improved modeling of the amount and/or quality of daylight. For example, when a building is designed from the inside to the outside, a user/owner may desire to obtain maximum daylighting which will impact the interior, then impact the glazing and wall construction (e.g., curtain walls or punched windows). The invention may provide information to facilitate reducing or eliminating solar related glare and/or vision problems from the daylight. For example, the window shade system may eliminate the use of screen fabric, and instead, incorporate a translucent fabric.

One or more fabric properties may affect the brightness factor. For example, each fabric has a known property that is affected by color, density, thickness, yarn opacity and/or the like. These properties include, for example, fabric reflectance, fabric absorption, visible light transmission, visible light reflectance, visible light absorbance, visible light transmittance, visible light diffusion (which may or may not be fabric surface brightness and illumination values) and/or the like. The present invention may be used to qualify, and quantify a fabric brightness factor associated with various types of fabric under various conditions.

The color of the fabric may also affect the brightness factor. For example, a light fabric color with 2% openness will be very different from a light fabric with 5% openness; however, a dark fabric with 5% openness may be similar to a light fabric with 2% openness. The brightness factor and the color of the fabric may also be used to derive the amount of heat that may be radiated off the fabric. For example, a dark fabric with 0.9 emissivity and 90% absorption may allow more long wave radiation to enter a room, while a light fabric with 0.9 emissivity and 10% absorption will allow less long wave radiation.

The present invention is described with respect to roller shade fabrics. In an exemplary embodiment, the invention may be applicable to woven screen fabrics with a vinyl coating over a polyester or fiberglass substrate. However, one skilled in the art will appreciate that a brightness factor may be calculated for any type of window covering such as, for example, translucent, transparent, cloth, cotton, polyester, rayon, nylon, linen, bamboo, wool, silk, satin, vinyl, TPO, polyolefin, fabrids, ThermoVeil® fabric (produced by MechoShade Systems, Inc. of New York), EuroVeil® fabric (produced by MechoShade Systems, Inc. of New York), EcoVeil™ fabric (produced by MechoShade Systems, Inc. of New York), allied shade cloths, fabric coverings with and/or without low E coatings, mesh, mesh coverings, window slats, metallic coverings, any combinations thereof, and/or the like.

The present invention may also be used to facilitate the measurement of the brightness value of horizontal louvers, vertical blinds, adjustable louvers, panels, slats and Venetian type blinds, fixed or operable to varying angles of incidence to the solar ray. Typical louvers may not have a standard openness factor. Rather, louvers are more closed as the tilt angle increases which may be considered its openness factor. Louvers of a particular color and tilt angle (with the solar ray normal to the glass at a given angle) have varying degrees of brightness over the surface of the blind. The louvers may include resultant factors of: louver reflectance, louver absorption, visible light transmission, visible light reflectance, visible light absorbance, visible light transmittance, visible light diffusion (which may or may not be louver surface brightness and illumination values) and/or the like. The present invention may be used to qualify and quantify a louver blind brightness factor associated with various types of louvers under various conditions at specific tilt angles with a specific amount of light behind the blinds.

In one exemplary embodiment, with respect to FIG. 1, a test chamber 100 is used to facilitate testing and/or validation of one or more window coverings. Test chamber 100 can be configured with one or more wall panels 102. In one embodiment, test chamber 100 includes a six-sided enclosure. Walls 102 can comprise any building material, including, for example polystyrene, plywood, drywall and the like.

In one embodiment, a front surface 104 of test chamber 100 has a substantially centered 2' by 2' opening 106 for mounting one or more window coverings 110 and/or admitting solar radiation. A back surface 108 of test chamber 100 can be configured with one or more panels 102. In one embodiment, one window covering is used and back surface 108 includes one panel. Panels 102, in turn, can be configured with mounting support 114 for an illuminance probe 116. Panels 102 may also be configured to be moveable in multiple directions (e.g., 1-6 directions) for facilitating adjustment of the distance of probe 116 to window covering 110, adjusting the relative angle of probe 116 to window covering 110 (adjustment of the angle may not be required in all validation procedures), and/or the like.

Test chamber 100 is fixed for a particular validation procedure, but for other validation procedures, test chamber 100 may be configured in a variety of ways. For example, with reference to an exemplary embodiment depicted in FIG. 2, test chamber 200 comprises panels 202 and is mounted on a stand 220 configured for six degrees of freedom (i.e., x, y, z, yaw, pitch and/or roll). Stand 220 can facilitate adjustment due to changing solar angles throughout a day and/or a year. In one embodiment, a mirror is used to reflect light rays into the opening on front surface 104 and the mirror is adjustable to account for the apparent motion of the sun in the sky.

Figure 2:
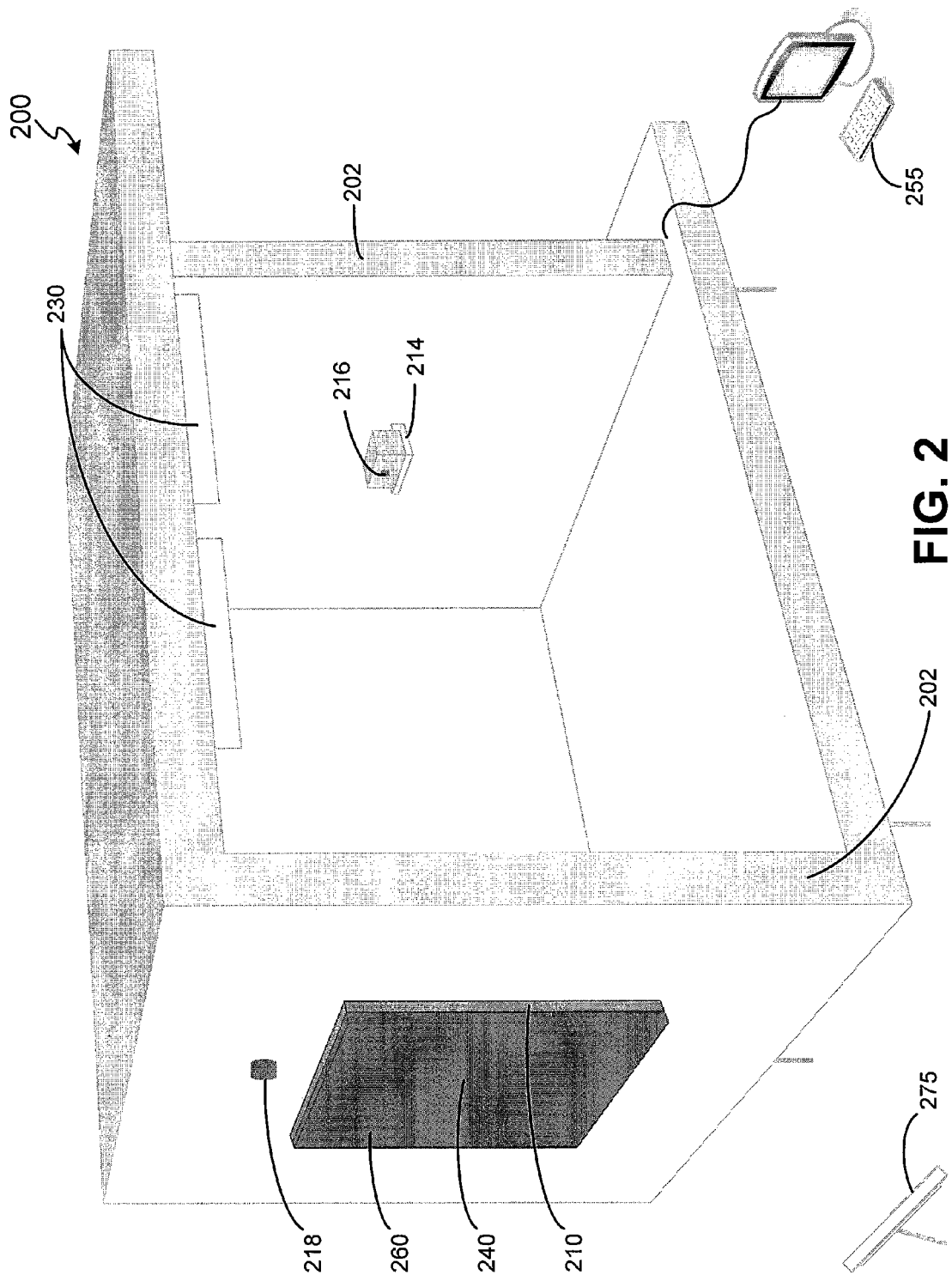
FIG. 2 is an exemplary test chamber mounted on a stand in accordance with an embodiment of the present invention.

The test chamber may also be painted to achieve the proper surface reflectance coefficient. With reference to FIG. 2, test chamber 200 may be painted in a variety of ways to facilitate fabric brightness testing. For example, in one embodiment, test chamber 200 is painted to achieve a proper surface reflection coefficient. In another embodiment, test chamber 200 is painted 50-50 gray to facilitate replication of ideal interior surface reflectivity conditions. In yet another embodiment, test chamber 200 is painted off-white to replicate typical office conditions.

The back of test chamber 200 is configured with a mounting support 214 for an illuminance probe 216. Illuminance probe 216 may be configured as any type of illuminance probe, such as, a Minolta™ or Tectronix™ narrow angle illuminance probe. Illuminance probe 216 is configured to take the illuminance readings of window covering 210 surface from a distance, and thus, minimizes errors due to the effect of self-shading and/or higher reflectivity of probe 216.

Test chamber 200 is configured with one or more lights 230 to facilitate studying the effect of indoor lighting on the surface brightness of window covering 210. For example, test chamber 200 can be configured with two lamps 230 mounted in one or more positions within chamber 200. While two lamps 230 are depicted, any number of lamps can be used to model the interior lighting conditions of a building. Lamps 230 may comprise fluorescent bulbs, halogen bulbs, tungsten-filament bulbs, and/or any other type of light bulb or bulbs used for interior lighting. Window covering 210 test samples are mounted in any position within test chamber 200.

In one exemplary embodiment, window covering 210 test samples are mounted on the inside of test chamber 200 in front of glazing 240.

In one embodiment, one or more diffusion filters 260 may be used to cover glazing 240 to provide a uniform light source. Diffusion filters 260 can be configured on any diffuse material such as, for example, a glazing light with a white ceramic coating, or translucent and/or semi-translucent acrylic sheets, because acrylic has the ability to diffuse light evenly throughout a surface. Diffusion filters 260 are also configured at any thickness to facilitate replication of overcast conditions. For example, in one embodiment, diffusion filter 260 is ⅛ inch thick. As a result, diffusion filter 260 acts as a secondary constant source.

A photometer 218 is mounted on a front surface panel 204 for facilitating recording the incident light level during the testing of window covering 210. Diffusion filters 260 are placed in front of the glass when the light is too strong for the meter. Photometer 218 is configured as any type of photometer, such as, for example, a Licor™ photometer. Photometer 218, in one embodiment, is placed in between diffusion filter 260 and glazing 240 to facilitate measuring the incoming solar radiation (light).

Test chamber 200 is configured to work with one or more computer simulation programs 255 to verify the results of the testing. Computer simulation programs 255 include commercial programs, such as, for example, Radiance and/or Lumen Micro.

Figure 3:
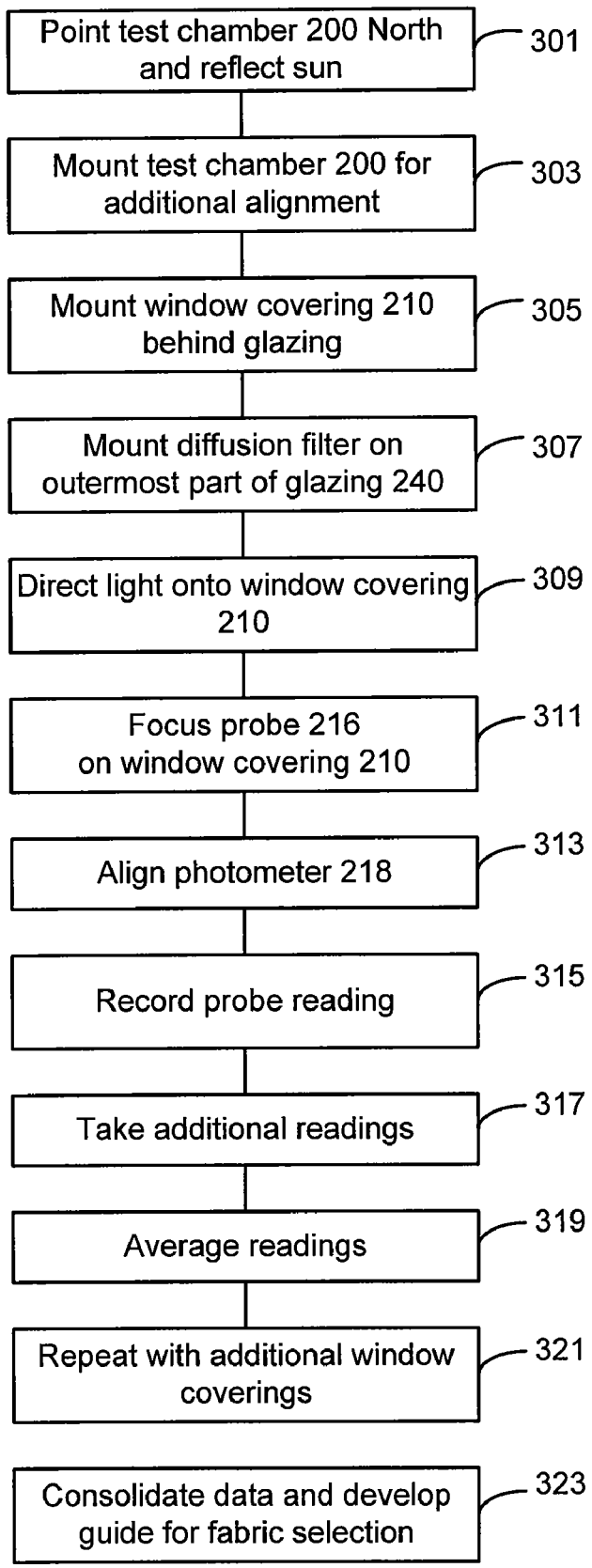
FIG. 3 is an exemplary method for measuring the outside luminance values and/or the illuminance on the inside window covering surface in accordance with an embodiment of the present invention.

Various methods for testing the surface brightness of window coverings 210 may be used. In one exemplary embodiment, and with reference to FIGS. 2 and 3, test chamber 200 is used to measure the outside luminance values and/or the illuminance of the inside window covering 210 surface. For example, test chamber 200 is first positioned facing north (step 301) in order to facilitate measurement of maximum daylighting. By pointing test chamber 200 to the north and using a mirror to reflect the light rays onto the face of the test chamber, front face 204 is aligned substantially perpendicular to the sun rays.

In another embodiment, if tilting and/or rotation of test chamber 200 does not result in test chamber 200 facing the sun at a substantially direct normal, test chamber 200 is mounted (step 303) for additional alignment. That is, test chamber 200 is mounted horizontal on a substantially level surface with front face 204 and window covering 210 facing north.

Next, window covering 210 to be tested is mounted flat behind glazing 240 (step 305). Window covering 210 is mounted in a frame, and it is hung and/or mounted in any other manner. Because the time of day and/or the season affect the window covering 210, variations of the outside illumination levels can fluctuate. That is, though the amount of sunshine perceivable to the human eye is apparently constant for a given duration of time, the actual measured illumination levels differ significantly. Accordingly, one or more diffusion filters 260 are mounted (step 307) on the outermost part of glazing 240 and/or adjacent to window covering 210. Diffusion filter 260 is used to facilitate balancing the illuminance by diffusing the light. Diffusion filter 260 has its optical properties measured beforehand and thus, the illumination received inside test chamber 200 through diffusion filter 250 is adjusted by a factor that accounts for the reduced light transmission from diffusion filter 260.

A mirror 275 is used to direct solar radiation (light) (step 309) onto the surface of window covering 210. Mirror 275 is configured to be any size to facilitate directing a constant beam of light incident on the surface of window covering 210, thereby reducing any errors in the measurement solar radiation into test chamber 200. In one embodiment, mirror 275 is larger than the front panel opening. For example, in one embodiment, mirror 275 is configured to be approximately 4 feet×4 feet. Mirror 275 is configured of any reflective type of surface, and in one embodiment, is configured to be substantially flat. In one exemplary embodiment, mirror 275 is a high quality flat mirror.

Next, illuminance probe 216 is focused on the center portion of window covering 210 (step 311) and initialized to record illuminance data. In order to measure SBV, photometer 218 is aligned and initialized to record the incident light behind diffusion filter 260 (step 313). A steady reading from illuminance probe 216 is recorded simultaneously with the reading from the photometer 218 (step 315). One or more additional readings are taken (step 317) to facilitate accurate measurements, as the measurements are averaged and processed in order to reduce measurement errors and calculate an accurate SBV (step 319). The same procedure is repeated to test additional window covering samples 210 (step 321).

Finally, the data is consolidated in order to develop a guide for fabric selection based on luminance and illuminance of surface brightness and the transmission factor of the glazing (step 323). For example, this information is used to create a Shade Cloth Brightness Guide ("SCBG"). The SCBG is used to provide a lighting consultant, interior architect/designer and/or building architect with the values they need to select the desired fabric. The SCGB information are combined with other interior design guides (for example, a guide for an openness factor), to facilitate optimization of an interior structure. In one embodiment, a customer may desire a certain color of fabric for his window coverings. In order to achieve the optimum interior brightness for the structure, the SCGB is consulted to determine the optimum density factor for the window coverings to achieve the desired interior brightness.

Once the data from photometer 218 and/or illuminance probe 216 has been recorded, the data can be processed and/or adjusted in order to determine a brightness value for window covering 210. For example, the data may be adjusted due to fluctuations from the incoming solar radiation (i.e., from cloud cover and/or the like). Further, adjustments may also be made for different types of glazing 240, interior reflectance coefficients, topography, ASHRAE sky models, geodesic coordinates of a building, actual and calculated solar position, actual and calculated solar angle, actual and calculated solar radiation, actual and calculated solar intensity, time, solar declination, solar altitude, solar azimuth, sky conditions, surface orientation of glazing 240, compass reading of glazing 240, the incidence angle of sun striking glazing 240, window covering 210 position, and/or the like.

The "standard" incident light level on a vertical was calculated by converting the standard thermal value of 248.3 Btu/hr.ft2 to foot candles (IP Units) and to lux (SI Units) by using a conversion value developed from the irradiation (thermal) and illumination (light) solar constants given in the IES Handbook. The solar irradiation constant is 1,350 W/m2 or 427.9 Btu/hr.ft2. The solar illumination constant is 128,000 lux or 11,891.6 foot candles. The invention includes a conversion value for converting Btu/hr.ft2 (total solar property) to an equivalent lighting level (visual property) using computer modeling analysis. Roller shade fabric luminance values are also plotted (along with a trend line) as a function of the brightness factor, for glazing units with visible transmittance values ranging from, in one embodiment, 10% to 90%. The luminance values for shade fabrics alone (without glazing lites) are determined by dividing the adjusted measured values by the visible light transmittances of each glazing lite that are mounted in front of the fabric samples.

During the testing of fabrics, slight changes in the source radiation (light) occurred due to adjusting the reflecting mirror, etc. To compare fabrics, all data is based on an equal source radiation value. In one embodiment, the average inside wall surface measurement, the "behind fabric" measurement and the fabric surface measurement are all "brought to unity" with the average outside light meter value. For example, the values are adjusted for the small variation in the source solar (light) radiation. In one embodiment, the fabric test data measurements are adjusted such that they are based on the average source light meter value. The true measured value is divided by the average values of the true measured values for a light source in order to obtain a multiplier. The multiplier is used to normalize and adjust the original measured values of the glazing and fabric.

Figure 4:
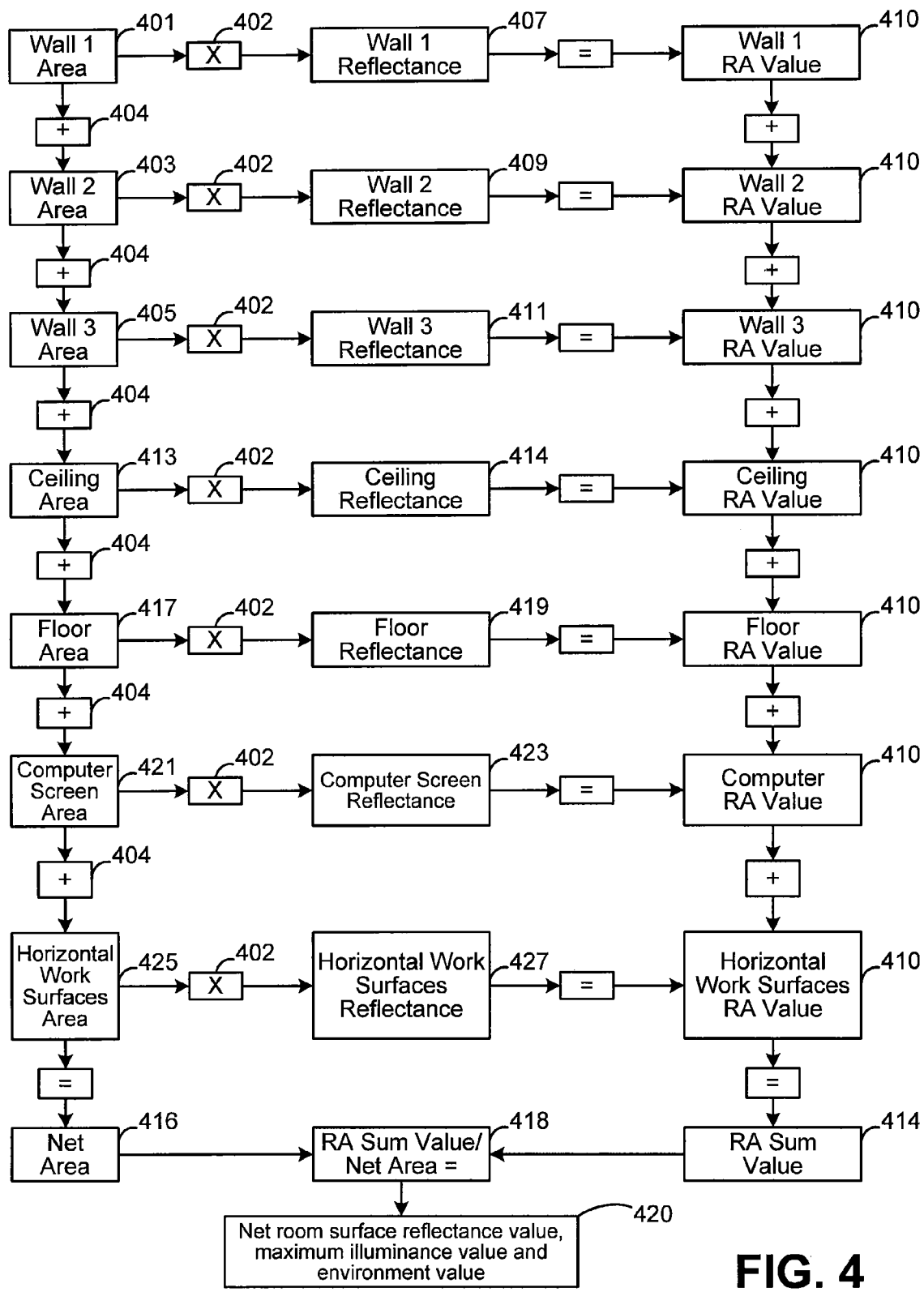
FIG. 4 is an exemplary method for calculating the net room surface reflectance value in accordance with an embodiment of the present invention.
Figure 5:
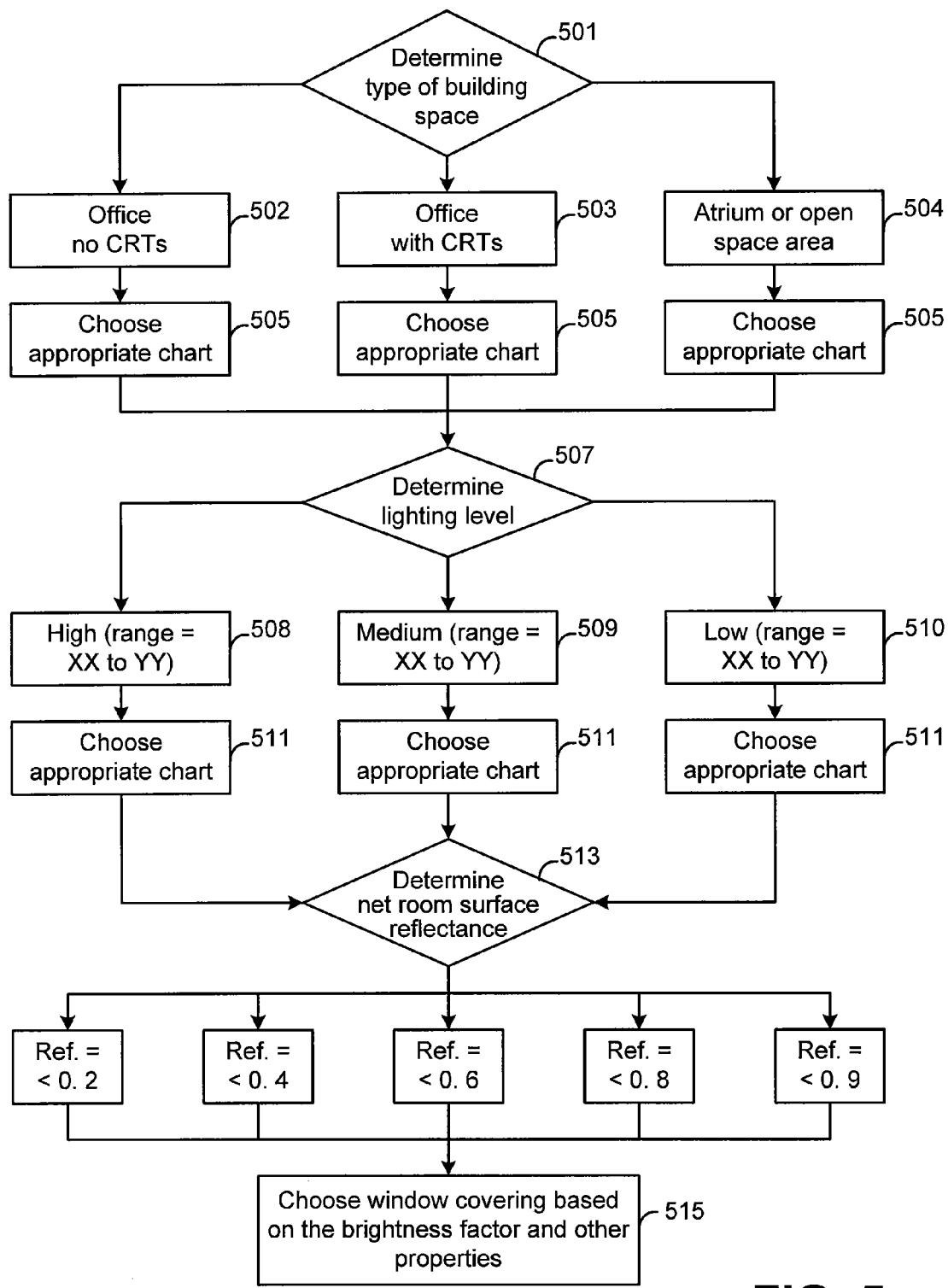
FIG. 5 is an exemplary method for determining the optimum shade surface brightness values in accordance with an embodiment of the present invention.

A professional may consider the net room surface reflectance when selecting a fabric having a particular brightness factor. With reference to FIGS. 4 and 5, exemplary methods for calculating the net room surface reflectance value are provided. With reference to FIG. 4, an exemplary method for calculating the net room surface reflectance value is illustrated. This calculation includes considering one or more wall areas (steps 401, 403, 405), wall reflectances (steps 407, 409, 411), ceiling area and reflectance (steps 413 and 415), the floor area and reflectance (steps 417, 419), the computer screen area and reflectance (step 421, 423), and the horizontal work surfaces area and reflectances (step 425, 427). This will provide the general room area and reflectance values.

In one embodiment, the illuminance of the CRT screen is used to determine the maximum illuminance acceptable with a window shading device under today's acceptable brightness standard (now 10:1, but subject to change). While the maximum illuminance value may include the orb of the sun, in the present embodiment, the orb of the sun is not included.

These room reflectance values are multiplied (steps 402) and/or added (steps 404) in order to find various reflectance areas (steps 410) and net areas (step 412). The sum of all the reflectance areas of the walls, ceiling and floor (step 414) are divided (step 418) by the total net area (step 416) to determine the maximum illuminance value and the environment value needed for the shaded window (step 420), which also determines the factors needed to select the fabric for the project based on the given parameters.

The amount of light penetrating into the room space is a factor of the visible properties of the glazing system and the shade fabric, if the shade is on the window. The glazing system visible properties and the shade fabric brightness value are considered when choosing the optimum roller shade fabric (step 430).

Once the threshold of brightness has been established, then the fabric brightness values needed for the project are determined. The fabric brightness values may be based on the type of room and the needs of the people within the room (i.e., based on the type of tasks or functions they are performing). For example, with reference to an exemplary method outlined in FIG. 5, optimum shade surface brightness values are determined by first determining the type of building space requirements based on occupant functionality because the needs often vary dramatically (step 501). By determining the type of building space requirements, a structure can be examined to determine if its requirements include an office (e.g., an office with no CRTs (step 502), or an office with CRTs (step 503)), an atrium or open space area (step 504), and relative brightness of the interior (e.g., walls, floor, ceiling, work surfaces and/or the like) to the brightness of the daylit window. While office spaces with and without CRTs and/or atriums are depicted, other building spaces can be considered, for example, lounges, conference rooms, executive areas, training areas, sleeping areas, lobbies, receptions, kitchens, dining areas, cafeteria, corridors in open plan, bathrooms and/or the like.

Next, the appropriate chart is chosen for optimizing interior lighting (step 505). These charts may be predetermined based on the brightness values, daylighting information, glare information and the like described herein. For example, the amount of light penetrating into the room is effected by the visible light transmission of the glass, as well as the brightness and transmission of the shade and glass combination. Thus, the different glass and shade combinations are used to find the appropriate brightness chart for optimizing interior illumination. The selection of the appropriate brightness factor may depend upon the occupancy, architecture, space design, color of interior elements (floor, furniture, etc) and/or the like.

The following steps may be performed by the lighting consultant. After an appropriate chart is chosen, the desired lighting level is determined for the interior space (step 507). The desired lighting levels include a high range (step 508), medium range (step 509), and/or a low range (step 510). Once the desired lighting level is determined, a second chart is chosen to help determine the appropriate features needed to achieve the desired lighting level (step 511), as desired by professional lighting designers. For example, the brightness factor for each fabric or the maximum brightness required for the interior occupancy may be considered in determining the appropriate features needed to achieve the desired lighting level. Next, the net room surface reflectance is calculated (step 513), so that an appropriate window covering 210 is chosen (step 515) based on the brightness factor desired.

In accordance with another exemplary embodiment, a two-stage glare calculation is used to calculate and/or model the interior glare of an interior space. The first stage of the glare calculation computes the locations, sizes and brightness of one or more light sources and/or the background luminance level. The second stage glare calculation computes a desired glare index. One or more programs are used to facilitate the glare calculation. For example, Findglare is used to locate one or more glare sources and calculates the background levels (indirect vertical illuminances) for a specified view field. Various glare formula calculations are used, such as, for example, the Guth visual comfort probability and the CIE glare index due to Einhom. One or more programs or scripts are also used to facilitate use of a glare program and/or formula calculations.

In another exemplary embodiment, an improved glare evaluation method is used to evaluate glare. The glare evaluation method includes both a standard monitoring protocol and advanced formulae. The equation used to calculate daylight glare $$G=0.48\Sigma L_s^{1.6}\Omega^{0.8}/L_b+(0.07\,\omega^{0.5}L_s)$$

Where:

$L_s$ is source luminance $L_b$ is background luminance $\omega$ is the solid angle sub tense of source at the eye.

$\Omega$ is the solid angle sub tense of the source modified for the position of its elements in different parts of the field of view.

The parameters in this glare evaluation method include the Window luminance (the source luminance), Adaptation luminance (the luminance of the surroundings including reflections from the internal surfaces), and/or the Exterior luminance (the luminance of the outdoors, caused by direct visible light, diffuse light from the sky and/or reflected light from the ground and other external surfaces).

In order to measure the daylight discomfort glare, one or more spot sensors (concentrated into a spot) are used to record continuous, automatic measurements of shielded and/or unshielded vertical illuminances. The vertical illuminances are from the glazing luminance, the adaptation luminance and/or the exterior luminance, and the vertical illuminance can be derived and the DGIn can be calculated. The sensors are mounted vertically on a tripod according to the midpoint of the glazing looking at its center. The sensor arrangement is due to the illuminance distribution with the glazing plane being non-uniform and therefore causes more glare than uniform light sources when positioned perpendicular to the line of sight. The glare sensation is largest at 0 degrees from the viewpoint.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. A method for determining a brightness factor for a fabric, said method comprising:

determining, using a light meter, an openness factor of said fabric;

determining, using said light meter, a visible light reflectance of an interior surface of said fabric;

determining, using said light meter, a visible light transmission of an interior surface of said fabric; and determining, by a computer, said brightness factor based upon said openness factor, said visible light reflectance, and said visible light transmission of said fabric.

2. The method of claim 1, wherein said of determining said openness factor comprises:

measuring, using said light meter, direct visible light through a blackened tube to obtain a direct visible light measurement; placing said fabric over a first end of said blackened tube;

placing said light meter at a second end of said blackened tube;

measuring, using said light meter, visible light through said fabric to obtain a fabric visible light measurement; and comparing said direct visible light measurement to said fabric visible light measurement to determine a reduction in visible light from said fabric.

3. The method of claim 1, wherein said of determining said visible light reflectance comprises:

measuring, using said light meter, direct visible light to obtain a direct visible light measurement;

pointing said light meter at said fabric;

measuring a reflectance of visible light off of said fabric to obtain a reflectance measurement; and comparing said direct visible light measurement to said reflectance measurement to determine a reduction in visible light from said fabric.

4. The method of claim 1, wherein said of determining said visible light transmission comprises:
    measuring, using said light meter, direct visible light through a tube to obtain a direct visible light measurement;
    placing said fabric over a first end of said tube;
    placing said light meter at a second end of said tube;
    measuring, using said light meter, visible light through said fabric to obtain a fabric visible light measurement; and
    comparing said direct visible light measurement to said fabric visible light measurement to determine a reduction in visible light from said fabric.

5. The method of claim 1, wherein said of determining said brightness factor further comprises subtracting, by said computer, said openness factor from said visual light transmission to obtain a fabric density property, then multiplying, by said computer, said fabric density property with said visible light reflectance, and then adding, by said computer, said openness factor.

6. The method of claim 1, further comprising comparing, by said computer, said brightness factor to a measured luminance value of said fabric.

7. The method of claim 1, further comprising comparing, by said computer, said brightness factor to a measured luminance value of said fabric having a light source in at least one of candela/m2 or FC.

8. The method of claim 1, further comprising comparing, by said computer, said brightness factor to a measured luminance value of said fabric having a light source in at least one of candela/m2 or FC and having a glazing.

9. The method of claim 1, further comprising selecting, by said computer, said fabric based upon said brightness factor and at least one of glazing properties, room properties or environmental conditions.

10. The method of claim 1, further comprising integrating said brightness factor with at least one of a shade control system, daylighting control system, daylight-brightness control system, daylighting prediction program, or building control system.

11. The method of claim 1, further comprising integrating said brightness factor with at least one of a shade control system, daylighting control system, daylight-brightness control system, daylighting prediction program, or building control system such that said control system overrides data based upon said brightness factor.

12. The method of claim 1, further comprising integrating said brightness factor with at least one of a shade control system, daylighting control system, daylight-brightness control system, daylighting prediction program, or building control system such that said control system only analyzes said brightness factor in response to the sun not significantly effecting a shading system associated with said fabric.

13. The method of claim 1, further comprising determining, by said computer, said brightness factor based upon a color of said fabric.

14. The method of claim 1, further comprising analyzing, by said computer, at least one of fluctuations from incoming solar radiation, different types of glazing, interior reflectance coefficients, topography, ASHRAE sky models, geodesic coordinates of a building, actual and calculated solar position, actual and calculated solar angle, actual and calculated solar radiation, actual and calculated solar intensity, time, solar declination, solar altitude, solar azimuth, sky conditions, surface orientation of said glazing, compass reading of said glazing, incidence angle of sun striking said glazing, or window covering position.

15. A method for comparing a surface brightness of a first fabric and a second fabric with a uniform light source to determine the relative brightness of said first fabric to said second fabric, said method comprising:
    determining, using a light meter, a first openness factor of said first fabric;
    determining, using said light meter, a second openness factor of said second fabric;
    determining, using said light meter, a first visible light reflectance of an interior surface of said first fabric;
    determining, using said light meter, a second visible light reflectance of an interior surface of said second fabric;
    determining, using said light meter, a first visible light transmission of an interior surface of said first fabric;
    determining, using said light meter, a second visible light transmission of an interior surface of said second fabric;
    determining, by a computer, a first brightness factor based upon said first openness factor, said first visible light reflectance, and said first visible light transmission of said first fabric;
    determining, by said computer, a second brightness factor based upon said second openness factor, said second visible light reflectance, and said second visible light transmission of said second fabric; and
    determining, by said computer, the relative brightness of said first fabric and said second fabric based upon said first brightness factor and said second brightness factor.

16. The method of claim 15, further comprising selecting, by said computer, a fabric with a lower brightness factor in response to a visible light reflectance of surrounding items being high.

17. The method of claim 15, further comprising selecting, by said computer, a fabric with a higher brightness factor in response to at least one of a visible light reflectance of surrounding items being low or a medium color value is being associated with said surrounding items.

18. A tangible computer-readable medium having stored thereon a plurality of computer-executable instructions that, if executed by a computing device, cause said computing device to perform a method for determining a brightness factor for a fabric, comprising:
    determining an openness factor of said fabric;
    determining a visible light reflectance of an interior surface of said fabric;
    determining a visible light transmission of an interior surface of said fabric; and
    determining said brightness factor based upon said openness factor, said visible light reflectance, and said visible light transmission of said fabric.

* * * * *

UNITED STATES PATENT AND TRADEMARK OFFICE
CERTIFICATE OF CORRECTION

PATENT NO. : 7,684,022 B2
APPLICATION NO. : 11/539559
DATED : March 23, 2010
INVENTOR(S) : Joel Berman et al.

It is certified that error appears in the above-identified patent and that said Letters Patent is hereby corrected as shown below:

In Column 14, Line 48, please delete "of".

In Column 14, Line 52, please insert a hard return before placing (placing should start a new paragraph).

In Column 14, Line 61, please delete "of".

In Column 15, Line 4, please delete "of" (second occurrence).

In Column 15, Line 16, please delete "of".

In Column 16, Line 44, please delete "is".

Signed and Sealed this

Twenty-seventh Day of April, 2010

David J. Kappos
*Director of the United States Patent and Trademark Office*